United States Patent [19]
Tokarski et al.

[11] Patent Number: 6,097,030
[45] Date of Patent: *Aug. 1, 2000

[54] METHODS AND APPARATUS FOR ADJUSTING EMISSION IMAGING SYSTEM DETECTOR ATTITUDE

[75] Inventors: Cheryl Tokarski, Prospect; Khurshid Afimiwala, Shelton, both of Conn.; Randy Schaefer, Waukesha, Wis.

[73] Assignee: General Electric Company, Milwaukee, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/937,391

[22] Filed: Sep. 25, 1997

[51] Int. Cl.⁷ .................................................. G01T 1/166
[52] U.S. Cl. .............................. 250/363.04; 250/363.05
[58] Field of Search .......................... 250/363.04, 363.05

[56] References Cited

U.S. PATENT DOCUMENTS

| | | | |
|---|---|---|---|
| 4,459,485 | 7/1984 | Span | 250/363.05 |
| 4,774,412 | 9/1988 | Kurkake | 250/363.05 |
| 4,961,208 | 10/1990 | Okada | 378/17 |
| 5,777,332 | 7/1998 | Lonn et al. | 250/363.05 |

*Primary Examiner*—Constantine Hannaher
*Attorney, Agent, or Firm*—John S. Beulick; Christian G. Cabou; Phyllis Y. Price

[57] ABSTRACT

An emission tomographic system which includes a gantry and a detector is described. The system automatically adjusts the detector attitude to maintain the detector at a desired orientation with respect to a patient during a scan. The system includes a tilt drive and processor coupled to the gantry and the detector. The processor receives signals indicative of changes in the gantry pitch angle, and uses such signals to determine appropriate changes in detector tilt. For each change in gantry pitch angle, the processor executes an algorithm relating gantry pitch angle to detector tilt angle, and determines an appropriate responsive change in detector tilt angle. The tilt drive then tilts the detector in accordance with the appropriate responsive change.

17 Claims, 3 Drawing Sheets

METHODS AND APPARATUS FOR ADJUSTING EMISSION IMAGING SYSTEM DETECTOR ATTITUDE

FIELD OF THE INVENTION

This invention relates generally to nuclear medical imaging and more particularly, to aligning a detector with a patient during a scan.

BACKGROUND OF THE INVENTION

In nuclear emission tomography, gamma cameras or detectors typically are used for locating and displaying human glands and organs and associated abnormalities. Abnormalities may be represented by higher uptake or lower uptake than the surrounding tissue. More specifically, and with respect to using a gamma camera, gamma-ray-emitting tracer material is administered to a patient, and the tracer material is more greatly absorbed by the organ of interest than by the other tissues. The gamma camera generates data, or an image, representing the distribution of such tracer material within the patient.

A gamma camera includes a multi-channel collimator and a gamma ray detector which converts energy from the gamma ray into an electrical signal which can be interpreted to locate the position of the gamma ray interaction in the planar detector. One known gamma ray detector which is commonly used is an Anger gamma camera, which is described in H. O. Anger, "Scintillation Camera", Rev. Sci. Instrum., Vol. 29, p. 159 (1958). Another known detector is a multi-crystal scintillation detector which has an array o)f small crystals coupled to an array of light detectors, which may be either photomultipliers or photodiodes. Yet another known detector is a solid-state position sensitive detector which converts energy from the gamma ray into an electrical charge which can be detected by an array of contacts.

The Anger gamma camera includes a large scintillation crystal responsive to radiation stimuli, i.e., gamma rays emitted by the patient. An array of photomultiplier tubes typically are optically coupled to the crystal. In operation, the gamma rays emitted by the patient in the direction of the detector are collimated onto the crystal, and each gamma ray which interacts with the crystal produces multiple light events. The multiple light events are detected by photomultipliers adjacent to the point of interaction. The photomultiplier tubes, in response to the light events, produce individual electrical outputs. The signals from the array of photomultipliers are combined using analog and digital circuitry to provide an estimate of the location of the gamma ray event. Further, analog and digital processing is used to produce more accurate position coordinates to form the acquired image.

More particularly, to generate an image, a representation of the distribution of events in the crystal is generated by utilizing a matrix of storage registers whose elements are in one-to-one correspondence with elemental areas of the crystal. The crystal elemental areas are identified by coordinates. Each time a light event occurs in the crystal, the event coordinates are identified and the register in the storage register matrix corresponding to the identified event coordinates is incremented. The contents of a given register in the matrix is a number that represents the number of events that have occurred within a predetermined period of time within an elemental area of the crystal. Such number is directly proportional to the intensity of radiation emitted from an elemental area of the radiation field. The number stored in the register therefore is used to establish the brightness of a display picture element corresponding to the crystal elemental area. The distribution of a radiation field is displayed in terms of the brightness distribution of the display.

In emission tomography, a plurality of such images are taken at various view angles around the organ of interest. Typically, in transaxial tomography, a series of images, or views, are taken at equal angular increments around the patient. The series of views around the patient are reconstructed to form transaxial slices, that is, slices across the axis of rotation. The process of acquiring the views and reconstructing the transaxial slices is termed emission computed tomography (ECT) or single photon emission computed tomography (SPECT).

Most detectors used for tomography are fixed to a large bearing which allows the detector to rotate about a fixed axis (roll axis) in order to acquire the views at different angles. A particular form of gantry, known as a ring stand, allows the detector to rotate and also swivel (tilt) and pitch in order to be able to image various organs in different patient attitudes. The ring stand can be used in connection with a patient table having its long axis parallel to the roll axis, and the detector can be brought close to the patient by adjusting the pitch axis.

The collimators used in known cameras and detectors have a multiplicity of holes through which gamma rays can pass. The holes are separated by dense material, typically lead, which attenuates the gamma rays and absorbs a large fraction of the gamma rays which impinge on the dense material. The dimensions of the openings and the thickness of the lead between the holes are selected to obtain an appropriate trade-off between resolution and sensitivity as well as to minimize the penetration through the walls of the holes. Typically, the collimators are exchangeable and the operator can select a most appropriate collimator for the imaging application and the energy of the gamma rays. The array of collimator holes are typically parallel with one another, but some collimators are arranged so that the openings converge at a line or point some distance from the collimator front surface so as to obtain some magnification of the patient.

Known multi-channel collimators used in emission imaging have an image resolution which degrades linearly with an increasing distance of the object from the collimator surface. It is beneficial, therefore, to acquire each view with the collimator as close to the patient as possible. To facilitate positioning of the collimator relative to the patient, the pitch axis may be adjusted to bring the detector either closer to or farther away from the patient.

For emission tomography imaging, in addition to positioning the collimator as close to the patient as possible, it is important to precisely control the detector attitude relative to the patient. Particularly, it is important to ensure that data be acquired with the collimator holes viewing substantially transverse to the axis of rotation. Incorrect detector attitude can result in degradation of image quality.

Although controlling detector attitude is important, it is difficult to monitor the detector attitude due to changes in gantry pitch. Particularly, as the gantry is pitched to adjust for a patient's size, the detector attitude relative to the patient changes. More specifically, when the pitch axis is changed, the direction of the collimator holes will change in the longitudinal direction by the same angle as the change in the arm angle. Therefore, after changing the gantry pitch, the detector tilt must be altered to properly position the detector for data acquisition.

One known method of maintaining proper detector attitude requires a system operator to manually tilt the detector to keep the detector at a desired orientation. However, such manual adjustment is both time consuming and cumbersome, particularly if the detector is unbalanced.

It would be desirable to automatically control detector attitude so that the detector is maintained in a desired orientation as the gantry is pitched. It also would be desirable to provide such control without significantly increasing the cost of the system.

SUMMARY OF THE INVENTION

These and other objects may be attained in a system which, in one embodiment, automatically adjusts the detector attitude to maintain the detector at a desired orientation with respect to a patient during a scan. In one embodiment, the system includes a tilt drive and position sensors coupled to the gantry and detector. The gantry position sensor generates electrical signals representative of gantry pitch angle. The detector position sensor generates electrical signals representative of detector tilt angle. A processor is coupled to the position sensors and the tilt drive.

In operation, the processor receives signals from the gantry position sensor. Such signals are indicative of changes in the gantry pitch angle. Using such signals, the processor determines appropriate changes in detector tilt. Specifically, for each change in gantry pitch angle, the processor executes an algorithm relating gantry pitch angle to detector tilt angle, and determines an appropriate responsive change in detector tilt angle. The processor then controls the tilt drive to tilt the detector in accordance with the appropriate responsive change.

With the system described above, to compensate for detector tilt displacement due to gantry pitch adjustment, the detector is tilted according to the adjusted gantry pitch. Particularly, when the gantry pitch angle changes, the detector is tilted in the opposite direction by the same amount as the change in gantry pitch angle.

The above described system enables precise and automated control of detector attitude. In addition, the system does not significantly increase the cost of the imaging system.

DETAILED DESCRIPTION

Figure 1:
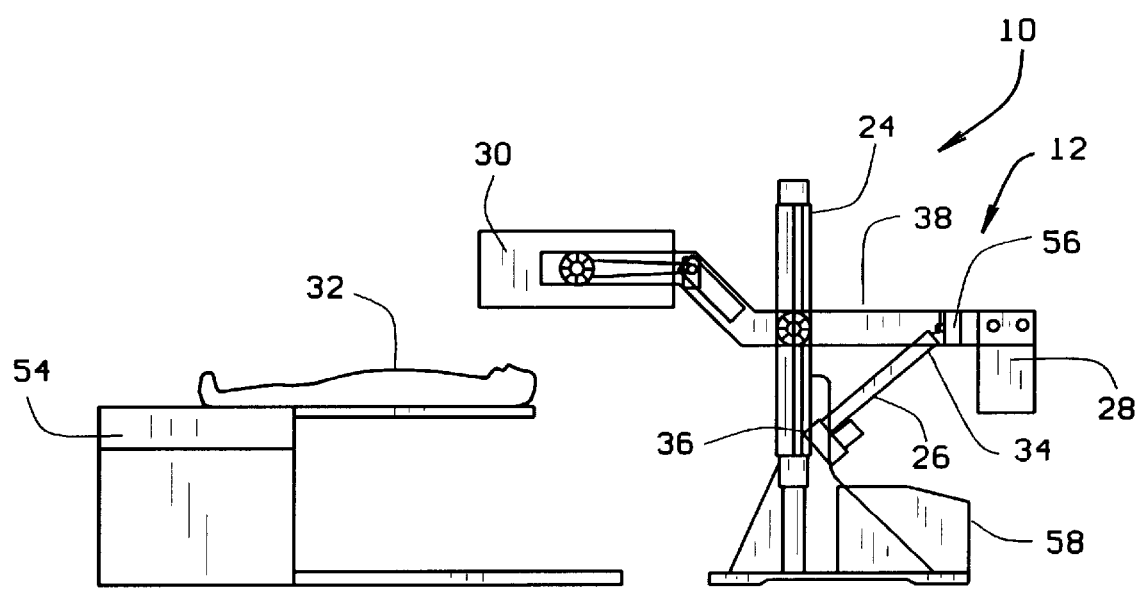
FIG. 1 is a perspective view of an emission tomography system.
Figure 2:
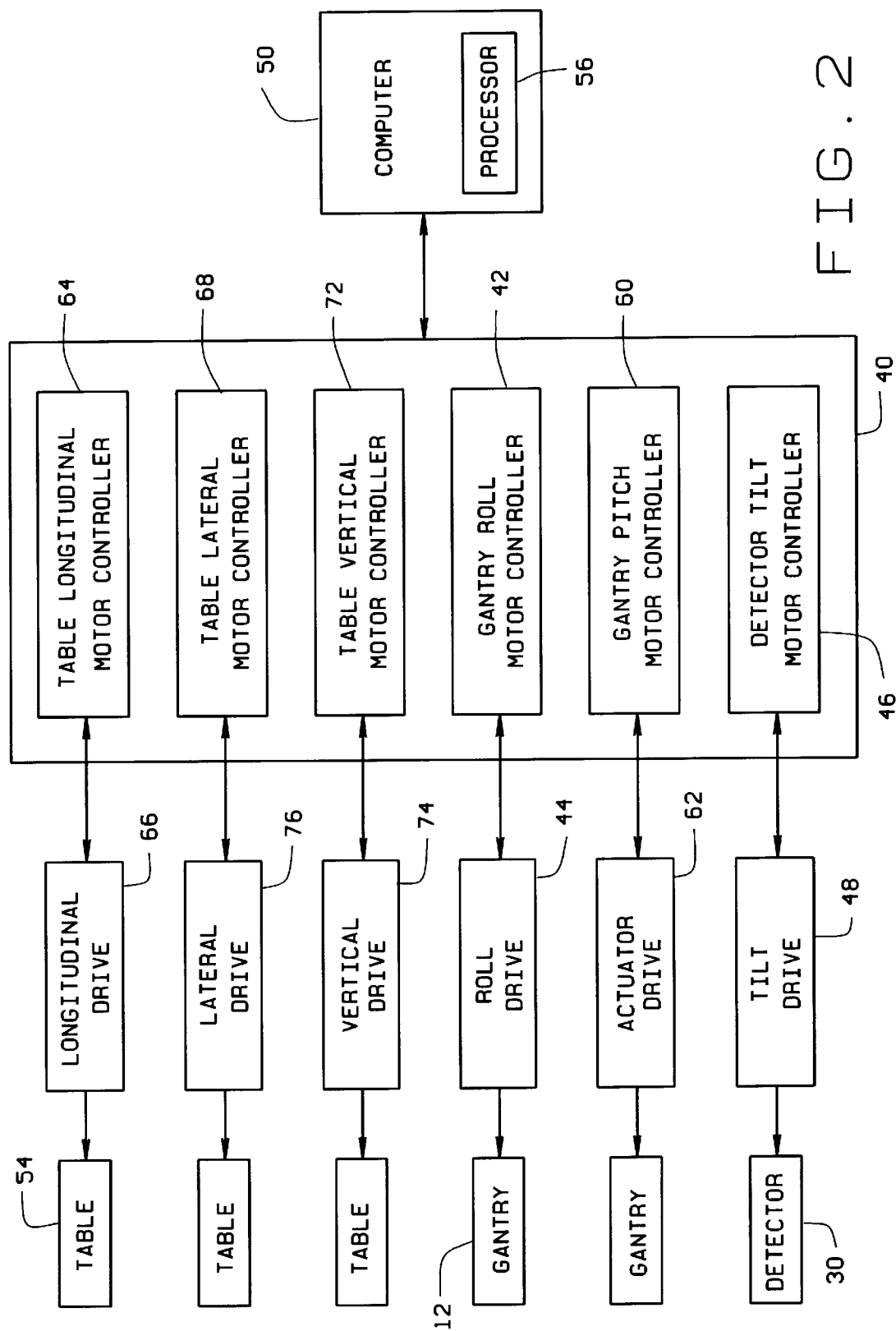
FIG. 2 is a block schematic diagram of the system illustrated in FIG. 1.

Referring to FIGS. 1 and 2, an emission tomography system 10 is shown as including a gantry casting 12 representative of a ring stand emission tomography system. Gantry 12 is a single piece casting structure which supports an inner circular ring bearing 24 for concentric relative motion.

Gantry 12 also includes an actuator 26, a counterweight 28, and a detector 30, or gamma camera, that detects gamma rays emitted by an object of interest, such as a medical patient 32. Actuator 26 has two ends 34 and 36. Actuator first end 34 is connected to a crossbar 56, and actuator second end is connected to the inner ring bearing 24. Detector 30, crossbar 56, and counterweight 28 are supported by arms 38. Actuator 26 changes the gantry pitch angle so as to position detector 30 at a desired position relative to patient 32. During a scan to acquire tomography data, inner circular ring bearing 24 and the components mounted thereto rotate about a center of rotation.

Detector 30 includes a collimator and a scintillation crystal, which operate in a well known manner. The scintillation crystal senses collimated gamma ray radiation emitted by patient 32 and produces electrical signals representing the intensity of received gamma rays. Detector 30 may, for example, be an Anger gamma camera or solid state position sensitive detector.

Rotation, tilt, and pitch of the detector 30 are governed by a control mechanism 40 inside an integrated power supply 58 of emission tomography system 10. Control mechanism 40 includes a gantry roll motor controller 42 and is coupled to roll drive 44 to control the rotational speed and angular position of gantry 12. Control mechanism 40 also includes a gantry pitch motor controller 60 and is coupled to the actuator drive 62 to control the gantry pitch angle. Control mechanism 40 also includes a detector tilt motor controller 46 and is coupled to the tilt drive 48 to control the detector tilt. A detector position sensor, such as a decoder, is coupled to tilt drive servo motor 48 and configured to generate signals representative of the detector tilt angle. Similarly, a gantry pitch sensor, such as a decoder, is coupled to the actuator drive servo motor 62 and configured to generate signals representative of the gantry pitch angle.

A computer 50 is coupled to the gantry pitch motor controller 42 and detector tilt motor controller 46 to provide control signals and information to actuator drive 62 and tilt drive 48. Computer 50 also is coupled to the detector position sensor and gantry pitch sensor to acquire position data, i.e., electrical signals, relating to the detector tilt angle and gantry pitch angle, respectively. In addition, computer 50 operates the table motor controllers 64, 68, and 72 which controls the table longitudinal drive 66, table lateral drive 70, and table vertical drive 74 to operate the table 54 and position the patient 32 relative to detector 30.

In operation, patient 32 receives an internal dose of radiopharmaceutical compounds which emit gamma ray energy, and is positioned on patient table 54. Patient table 54 is positioned along the central longitudinal axis of gantry 12, also referred to herein as the center of gantry rotation. Detector 30 is positioned so that it is close to patient 32 and is tangent to the orbital path traced by rotating detector 30 without interfering with patient 32 or table 54. To move detector 30 closer or farther from the patient/table, gantry arms 38 are pitched in or out. Particularly, computer 50 activates gantry pitch motor controller 60 and actuator drive 62 to pivot the arms 38 about a pitch axis 76 so that the detector 30 moves closer or farther from patient 32. In addition, computer 50 activates detector tilt drive controller 46 and tilt drive 48 to position detector 30 so that it is substantially parallel with the longitudinal axis of the gantry 12, also referred to herein as the center of rotation. Particularly, it is important to ensure that data be acquired with the collimator substantially transverse to the gantry axis of rotation. Incorrect detector attitude can result in degradation of image quality. As used herein, detector attitude refers to detector position relative to the longitudinal axis of the gantry 12.

Figure 3:
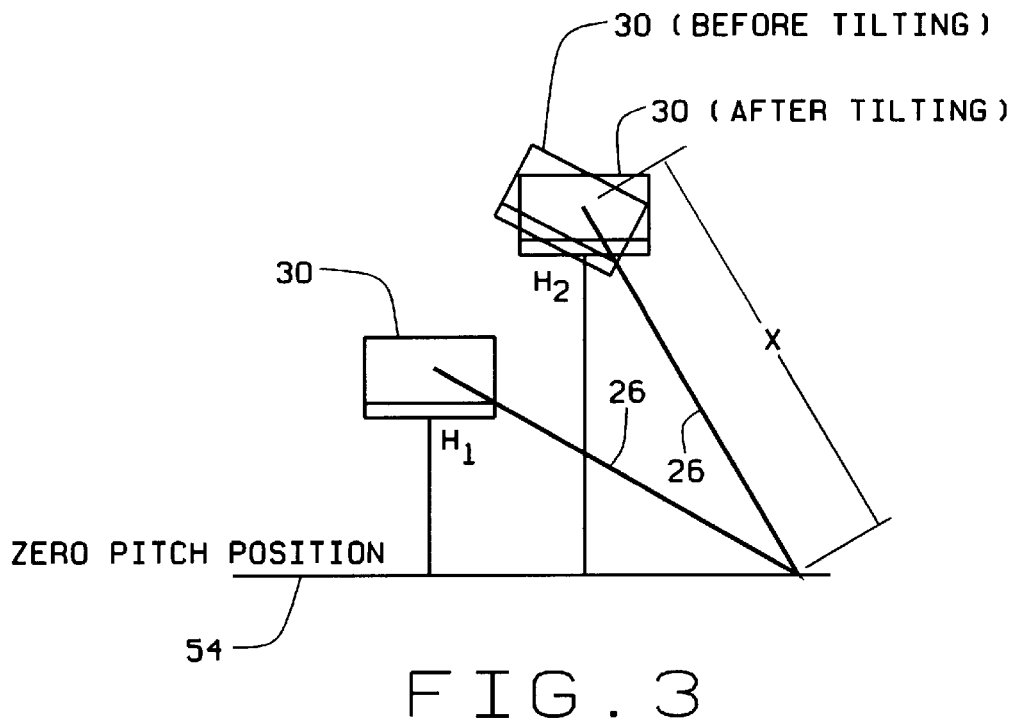
FIG. 3 illustrates detector tilt displacement associated with changes gantry pitch angle.

FIG. 3 illustrates detector tilt displacement associated with changes in gantry pitch angle when actuator 26 has a length (x). As detector 30 pitches in and out relative to the table 54, e.g., between a height H1 and height H2, detector 30 changes angles with respect to table 54, and thus the center of gantry rotation. Particularly, detector 30 moves out of a parallel orientation with the longitudinal axis, hence altering the detector attitude with respect to the patient.

In accordance with one embodiment of the present invention, detector 30 is automatically tilted in response to changes in gantry pitch. Particularly, computer 50 includes a processor 56 programmed to determine gantry pitch angles and to activate tilt drive 48 to tilt detector 30 to appropriate detector tilt angles. More specifically, processor 56 receives position indicating signals from the gantry pitch servo motor sensor so that processor 56 may identify each change in gantry pitch angle. For each identified change in gantry pitch angle, processor 56 determines an appropriate responsive change in detector tilt angle so that the desired detector attitude is maintained. Specifically, processor 56 analyzes the position indicating signals and determines the appropriate responsive change in detector tilt angle in accordance with:

$$\Delta(\text{tilt angle change}) = -\Delta(\text{gantry pitch angle change}). \quad (1)$$

Processor 56 then provides control signals to detector controller 46 and tilt drive 48 so that the tilt drive 48 tilts detector 30 in accordance with the determined change in detector tilt angle. When the gantry pitch angle changes, therefore, detector 30 is tilted in the opposite direction by the same amount as the change in gantry pitch angle.

Figure 4:
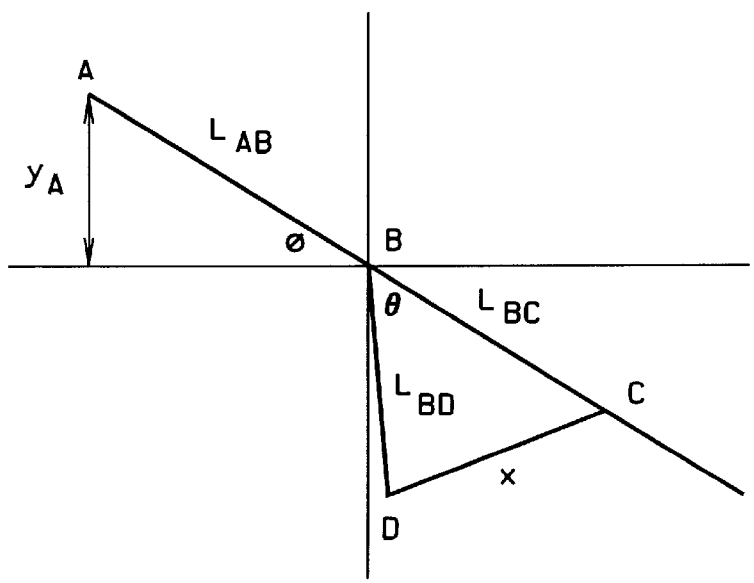
FIG. 4 is a schematic illustration showing the angular relationship between the actuator and the detector shown in FIG. 1.

FIG. 4 is a schematic illustration showing the angular relationship between actuator 26 and detector 30. Processor 56 is programmed to identify each change in gantry pitch angle (φ) in accordance to the relative positions of gantry arm 38, actuator 26, and detector 30. Particularly, and as shown, when gantry arm 38 is pitched at gantry pitch angle (φ) with respect to the center of gantry rotation, then:

$$d\theta/dx = x/[L_{BC} * L_{BD} * \sin(\theta)];$$

$$\Delta(\phi) = -\Delta(\theta);$$

and $$y_A = L_{AB} \sin(\phi); \quad (2)$$

where:
x=an actuator length,
$y_A$=distance of the tilt axis from the center of gantry rotation,
$L_{AB}$=distance between the tilt axis and the pitch axis,
$L_{BC}$=distance between the pitch axis and the actuator connection to at the counterweight,
$L_{BD}$=distance between the pitch axis and the actuator connection to the gantry,
θ=angle between $L_{BD}$ and $L_{BC}$, and
φ=pitch angle between $L_{AB}$ and the center of gantry rotation.

As explained above, processor 56 is coupled to gantry 12 and configured to receive signals indicative of the pitch angle (φ). Particularly, when gantry 12 is pitched, processor 56 identifies a change in gantry pitch angle in accordance with the relationship described above in equation (2).

Processor 56 is further configured to determine an appropriate change in detector tilt angle for each change in gantry pitch angle. Processor also is coupled to detector controller 46 and tilt drive 48 so that tilt drive 48 activates and tilts detector 30 in accordance with the determined charge in detector tilt angle. More specifically, tilt drive 48 and actuator drive 62 are synchronously coupled with processor 56 so that closed loop digital servo conltrol with position feedback may be used to maintain detector attitude as gantry arm 38 is pitched. The coupling between actuator drive 62 and tilt drive 48 may, however, be disabled to operate drives 62 and 48 independently.

In accordance with one embodiment, a low backlash modular worm gear box is used in tilt drive 48. Particularly, the worm gear is attached to a drive shaft of tilt drive 48, and is coupled to a planetary gear box driven by the servo motor. The modular worm gear box increases detector lilt accuracy, and overcomes detector unbalance. The worm gear box also is adapted to fit the tilt drive in a small enclosure, and provides the 90 degree drive required for detector 30.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the gantry described herein is a ring stand gantry in which both the gantry includes two circular rings. Many other gantries may be used. Accordingly, the spirit and scope of the invention are to be limited only by the terms of the appended claims.

We claim:

1. An emission imaging system for imaging an object of interest, said system comprising a gantry having a detector secured thereto, a patient table, and a computer coupled to the gantry and to the detector to detect and control the position of the detector relative to the table, said detector including a collimator, said computer programmed to:
    control gantry pitch to position said detector at a desired position relative to said object of interest; and
    control detector tilt based on the gantry pitch so that a face of said collimator is substantially parallel with the detector axis of rotation.

2. An emission imaging system in accordance with claim 1 further comprising a tilt drive coupled to said detector for tilting said detector about a tilt axis, and a gantry drive for pitching said gantry about a pitch axis.

3. An emission imaging system in accordance with claim 1 wherein to control detector tilt, said computer is further programmed to determine a gantry pitch angle and to determine a detector tilt angle using the determined gantry pitch angle.

4. An emission imaging system in accordance with claim 3 wherein said computer is further programmed to generate a control signal to move the detector to the determined detector tilt angle.

5. An emission imaging system in accordance with claim 3 wherein said computer is further programmed to identify a change in gantry pitch angle, and determine a change in detector tilt angle in accordance with:

Δ(detector tilt angle change)=−Δ(gantry pitch angle change).

6. An emission imaging system in accordance with claim 5 further comprising an actuator having two ends, said actuator connected at one of said ends to a crossbar and at said other end to an inner ring bearing, and wherein said computer is programmed to identify a change in gantry pitch angle in accordance with:

$$d\theta/dx = x/[L_{BC} * L_{BD} * \sin(\theta)];$$

$$\Delta(\phi) = -\Delta(\theta);$$

and $$y_A = L_{AB} \sin(\phi);$$

where:
x = the actuator length,
$y_A$ = a distance of a tilt axis from a center of gantry rotation,
$L_{AB}$ = a distance between the tilt axis and a pitch axis,
$L_{BC}$ = a distance between the pitch axis and the actuator connection to the counterweight,
$L_{BD}$ = distance between the pitch axis and the actuator connection to the gantry,
θ = an angle between $L_{BD}$ and $L_{BC}$, and
φ = the pitch angle between $L_{AB}$ and the center of gantry rotation.

7. A method for performing a scan of an object with an emission imaging system including a gantry having a detector secured thereto, a patient table, and a processor coupled to the gantry and to the detector to detect and control the position of the detector relative to the table, said method comprising the steps of:
determining a gantry pitch angle; and
determining a detector tilt angle based on the determined gantry pitch angle.

8. A method in accordance with claim 7 further comprising the step of moving the detector to the determined detector tilt angle.

9. A method in accordance with claim 7 wherein determining the detector tilt angle comprises the steps of identifying a change in gantry pitch angle, and determining a change in detector tilt angle in accordance with:

Δ(detector tilt angle change)=−Δ(gantry pitch angle change).

10. A method in accordance with claim 9 wherein the emission imaging system further includes an actuator having two ends, the actuator connected at one end to a crossbar and at the other end to an inner ring bearing, and wherein identifying a change in gantry pitch angle comprises determining:

$$d\theta/dx = x/[L_{BC} * L_{BD} * \sin(\theta)];$$

$$\Delta(\phi) = -\Delta(\theta);$$

and $$y_A = L_{AB} \sin(\phi);$$

where:
x = the actuator length,
$y_A$ = a distance of a tilt axis from a center of gantry rotation,
$L_{AB}$ = a distance between the tilt axis and a pitch axis,
$L_{BC}$ = a distance between the pitch axis and the actuator connection to the counterweight,
$L_{BD}$ = distance between the pitch axis and the actuator connection to the gantry,
θ = an angle between $L_{BD}$ and $L_{BC}$, and
φ = the pitch angle between $L_{AB}$ and the center of gantry rotation.

11. A method in accordance with claim 7 wherein the emission imaging system further includes a gantry actuator drive coupled to the gantry, a tilt drive coupled to the detector, a gantry position sensor for generating signals representative of a gantry pitch angle, and a detector position sensor for generating signals representative of a detector tilt angle, wherein the processor is coupled to the position sensors and the tilt drive, and wherein the step of determining a gantry pitch angle comprises:
pitching the gantry; and
analyzing signals generated by the gantry position sensor.

12. A method in accordance with claim 7 further comprising the step of performing a tomographic scan of the object.

13. A processor for an emission imaging system including a gantry having a detector secured thereto, a patient table, said processor coupled to the gantry and to the detector for detecting and controlling the position of the detector relative to the table, said processor configured to:
determine a gantry pitch angle; and
determine a detector tilt angle based on the determined gantry pitch angle.

14. A processor in accordance with claim 13 further configured to move the detector to the determined detector tilt angle.

15. A processor in accordance with claim 13 wherein to determine the detector tilt angle, said processor is configured to identify a change in gantry pitch angle, and to determine a change in detector tilt angle in accordance with:

Δ(detector tilt angle change)=−Δ(gantry pitch angle change).

16. A processor in accordance with claim 15 wherein the emission imaging system further includes an actuator having two ends, the actuator connected at one end to a crossbar and at the other end to an inner ring bearing, and wherein to identify a change in gantry pitch angle, said processor is configured to determine:

$$d\Theta/dx = x/[L_{BC}/L_{BD} * \sin(\Theta)];$$

$$\Delta(\phi) = -\Delta(\Theta);$$

and $$y_A = L_{AB} \sin(\theta);$$

where:
x = the actuator length,
$Y_A$ = a distance of a tilt axis from a center of gantry rotation,
$L_{AB}$ = a distance between the tilt axis and a pitch axis,
$L_{BC}$ = a distance between the pitch axis and the actuator connection to the counterweight,
$L_{BD}$ = distance between the pitch axis and the actuator connection to the gantry,
Θ = an angle between $L_{BD}$ and $L_{BC}$, and
φ = the pitch angle between $L_{AB}$ and the center of gantry rotation.

17. A processor in accordance with claim 13 wherein the emission imaging system further includes a gantry actuator drive coupled to the gantry, a tilt drive coupled to the detector, a gantry position sensor for generating signals representative of a gantry pitch angle, and a detector position sensor for generating signals representative of a detector tilt angle, wherein said processor is coupled to the position sensors and the tilt drive, and wherein to determine the gantry pitch angle, said processor is configured to analyze signals generated by the gantry position sensor.

\* \* \* \* \*